(12) United States Patent
Sato et al.

(10) Patent No.: US 11,515,024 B2
(45) Date of Patent: Nov. 29, 2022

(54) BLOOD PRESSURE MEASUREMENT DEVICE, MEDICATION MANAGEMENT METHOD, AND NON-TRANSITORY STORAGE MEDIUM STORING MEDICATION MANAGEMENT PROGRAM

(71) Applicant: OMRON HEALTHCARE Co., Ltd., Kyoto (JP)

(72) Inventors: Hironori Sato, Kyoto (JP); Mitsuharu Konishi, Kyoto (JP); Seisuke Fujiwara, Kyoto (JP); Daisuke Nozaki, Kyoto (JP)

(73) Assignee: OMRON HEALTHCARE CO., LTD., Kyoto (JP)

( * ) Notice: Subject to any disclaimer, the term of this patent is extended or adjusted under 35 U.S.C. 154(b) by 347 days.

(21) Appl. No.: 16/895,044

(22) Filed: Jun. 8, 2020

(65) Prior Publication Data

US 2020/0303050 A1 Sep. 24, 2020

Related U.S. Application Data

(63) Continuation of application No. PCT/JP2018/046237, filed on Dec. 17, 2018.

(30) Foreign Application Priority Data

Dec. 20, 2017 (JP) .............................. JP2017-243597

(51) Int. Cl.
*G16H 20/10* (2018.01)
*G16H 40/67* (2018.01)
(Continued)

(52) U.S. Cl.
CPC ............. *G16H 20/10* (2018.01); *A61B 5/022* (2013.01); *A61B 5/02141* (2013.01);
(Continued)

(58) Field of Classification Search
CPC ........ G16H 20/10; G16H 10/60; G16H 40/67; G16H 50/20; G16H 50/30; G16H 10/00;
(Continued)

(56) References Cited

U.S. PATENT DOCUMENTS

| 2004/0167408 | A1* | 8/2004 | Ashida | ................... | G16H 10/60 |
| | | | | | 206/538 |
| 2014/0316813 | A1* | 10/2014 | Bauer | ................... | G16H 15/00 |
| | | | | | 705/3 |

(Continued)

FOREIGN PATENT DOCUMENTS

| JP | 2004-105397 A | 4/2004 |
| JP | 2004-181137 A | 7/2004 |

(Continued)

OTHER PUBLICATIONS

International Preliminary Report on Patentability and Written Opinion of the International Searching Authority dated Jun. 23, 2020 in International (PCT) Patent Application No. PCT/JP2018/046237.

(Continued)

*Primary Examiner* — Omar Casillashernandez
(74) *Attorney, Agent, or Firm* — Wenderoth, Lind & Ponack, L.L.P.

(57) ABSTRACT

The present invention provides a technology that allows a user to more easily record medication information. A blood pressure measurement device according to an aspect of the present invention includes a prescription information acquisition unit configured to acquire prescription information, a preparatory action determination unit configured to determine whether a preparatory action for blood pressure measurement is performed, a blood pressure measurement operation unit configured to perform a blood pressure measurement operation in a case where an operation button is operated with the preparatory action determined to be performed, and a medication recording and processing unit (Continued)

configured to, in a case where the operation button is operated with the preparatory action determined not to be performed, assess that the operation is a medication confirmation operation, and generate and record medication information on the basis of the prescription information thus acquired.

20 Claims, 11 Drawing Sheets

(51) Int. Cl.
| | | |
|---|---|---|
| *G16H 10/60* | (2018.01) | |
| *G16H 50/30* | (2018.01) | |
| *G16H 50/20* | (2018.01) | |
| *A61B 5/021* | (2006.01) | |
| *A61B 5/022* | (2006.01) | |

(52) U.S. Cl.
CPC ............ *G16H 10/60* (2018.01); *G16H 40/67* (2018.01); *G16H 50/20* (2018.01); *G16H 50/30* (2018.01)

(58) Field of Classification Search
CPC ... A61B 5/02141; A61B 5/022; A61B 5/7475; A61J 7/04
USPC ........................................................ 600/490
See application file for complete search history.

(56) References Cited

U.S. PATENT DOCUMENTS

| | | | |
|---|---|---|---|
| 2016/0189317 A1* | 6/2016 | Papandrea ............ | G16H 10/60 |
| | | | 705/319 |
| 2017/0340293 A1* | 11/2017 | Al-Ali .................... | A61B 5/743 |

FOREIGN PATENT DOCUMENTS

| | | |
|---|---|---|
| JP | 2009-189485 A | 8/2009 |
| JP | 2010-213785 A | 9/2010 |
| JP | 2012-152520 A | 8/2012 |
| JP | 2015-195951 A | 11/2015 |
| JP | 2016-168243 A | 9/2016 |

OTHER PUBLICATIONS

International Search Report of the International Searching Authority for PCT/JP2018/046237 dated Feb. 19, 2019.

English translation of International Search Report of the International Searching Authority for PCT/JP2018/046237 dated Feb. 19, 2019.

* cited by examiner

| TYPE | TIME PERIOD | DOSE |
|---|---|---|
| MEDICINE A | MORNING | 1 TABLET |
| MEDICINE B | MORNING, EVENING | 2 TABLET |
| MEDICINE C | BEFORE BED | 3 TABLET |

FIG. 9

| DRUG | DATE AND TIME | DOSE |
|---|---|---|
| MEDICINE A | 2017/10/5 7:20 | 1 TABLET |
| MEDICINE B | 2017/10/5 7:20 | 2 TABLET |
| MEDICINE B | 2017/10/5 19:15 | 2 TABLET |
| MEDICINE C | 2017/10/5 22:10 | 2 TABLET |

FIG. 10

BLOOD PRESSURE MEASUREMENT DEVICE, MEDICATION MANAGEMENT METHOD, AND NON-TRANSITORY STORAGE MEDIUM STORING MEDICATION MANAGEMENT PROGRAM

This is a continuation of International application 2017-243597 with an international filing date of Dec. 20, 2017, and International Application PCT/JP2018/046237, with an international filing date of Dec. 17, 2018, filed by applicant, the disclosure of which is hereby incorporated by reference in its entirety.

TECHNICAL FIELD

The present invention relates to a blood pressure measurement device, a medication management method, and a non-transitory storage medium storing a medication management program.

BACKGROUND ART

A medication management device may be used to manage medication information on a user. Such a medication management device is proposed in JP 2015-195951 A. The medication management device in JP 2015-195951 A includes a touch panel display, and a medication recording screen is displayed on this touch panel display. Medicine buttons corresponding to medicines to be taken are displayed on the medication recording screen and, upon taking a medicine, the user selects and presses the applicable medicine button on the touch panel display. The selected medicine is recorded as medication information. As a result, medication information can be recorded relatively easily.

SUMMARY OF INVENTION

In a case where a medicine button displayed on a touch panel display as in the device described in JP 2015-195951 A is pressed, medication information can be recorded relatively easily.

Nevertheless, for users unfamiliar with touch panel displays, such as the elderly, the above-described operations are not easy. Such a user may be confused by, for example, the operations performed to display the medicine buttons on the touch panel display, a pressed position of a displayed button, and the like. As a result, the user cannot operate the device, and this makes it difficult to record the medication information.

The present invention, according to one aspect, has been made with reference to such circumstances, and an object of the present invention is to provide a technology that allows a user to more easily record medication information.

To solve the problems described above, the present invention adopts the following configuration.

That is, a blood pressure measurement device according to an aspect of the present invention is a blood pressure measurement device including an operation button, and the blood pressure measurement device includes a prescription information acquisition unit configured to acquire prescription information, a preparatory action determination unit configured to determine whether a preparatory action for blood pressure measurement is performed, a blood pressure measurement operation unit configured to perform a blood pressure measurement operation in a case where the operation button is operated with the preparatory action determined to be performed, and a medication recording and processing unit configured to, in a case where the operation button is operated with the preparatory action determined not to be performed, assess that the operation is a medication confirmation operation, and generate and record medication information on the basis of the prescription information thus acquired.

According to the configuration described above, in the case where the operation button is operated with the preparatory action for blood pressure measurement not having been performed, the operation is assessed as the medication confirmation operation. Then, the medication information is generated and recorded on the basis of the acquired prescription information. Accordingly, a user can easily record the medication information by simply operating the operation button of the blood pressure measurement device with the preparatory action for blood pressure measurement not having been performed.

In the blood pressure measurement device according to the aspect described above, in a case where the blood pressure measurement device includes a cuff, the preparatory action determination unit determines whether the preparatory action for blood pressure measurement is performed by use or non-use of the cuff. According to the configuration described above, it is possible to determine whether the operation is the blood pressure measurement operation or the medication confirmation operation by use or non-use of the cuff.

In the blood pressure measurement device according to the aspect described above, in a case where the blood pressure measurement device includes a power button, the preparatory action determination unit determines whether the preparatory action for blood pressure measurement is performed by operation or non-operation of the power button. According to the configuration described above, it is possible to determine whether the operation is the blood pressure measurement operation or the medication confirmation operation by operation or non-operation of the power button.

In the blood pressure measurement device according to the aspect described above, the medication recording and processing unit determines a time period of medication confirmation information input by operation of the operation button, read prescription drug information corresponding to the time period from the prescription information, and record the medication information on the basis of the medication confirmation information and the prescription drug information. According to the configuration described above, in accordance with the time period of input of the medication confirmation information, the prescription drug information on the corresponding time period is read and the medication information is recorded. In this way, easy recording of the medication information is achieved.

In the blood pressure measurement device according to the aspect described above, the blood pressure measurement device further includes a medication display control unit configured to, in a case where a medication time period is reached with the medication confirmation operation determined not to be performed, control display of a medication message that prompts medication. According to the configuration described above, it is possible to prevent the user from forgetting medication itself.

In the blood pressure measurement device according to the aspect described above, the medication recording and processing unit records medication omission information in a case where the medication confirmation operation is not performed by an end of the medication time period. According to the configuration described above, it is possible to record a case where the blood pressure is sufficiently low (within a standard range) and the user refrains from medication.

In the blood pressure measurement device according to the aspect described above, the medication recording and processing unit calculates a remaining amount of a prescription drug on the basis of the medication information. According to the configuration described above, the remaining amount of the prescription drug can be managed on the basis of the medication information.

In the blood pressure measurement device according to the aspect described above, the blood pressure measurement device further includes a medication information transmission unit configured to transmit the medication information to an external device. According to the configuration described above, the medication information can be transmitted to a user terminal and to an external server, and the medication information can be used for various purposes.

According to the present invention, it is possible to provide a technology that allows a user to more easily record medication information.

BRIEF DESCRIPTION OF DRAWINGS

FIG. 9 is a drawing illustrating an example of prescription information according to an embodiment.

FIG. 10 is a drawing illustrating an example of medication information according to an embodiment.

DESCRIPTION OF EMBODIMENTS

An embodiment according to an aspect of the present invention (hereinafter, also referred to as "the present embodiment") will be described below with reference to the drawings. However, the present embodiment described below is merely illustrative of the invention in all respects. Of course, various modifications and variations can be made without departing from the scope of the present invention. That is, specific configurations according to the embodiment may be adopted as appropriate in the implementation of the present invention. Note that although data appearing in the present embodiment will be described using natural language, the data is more specifically designated by pseudo-language, commands, parameters, machine language, and the like that are recognizable by a computer.

1 Application Example

Figure 1:
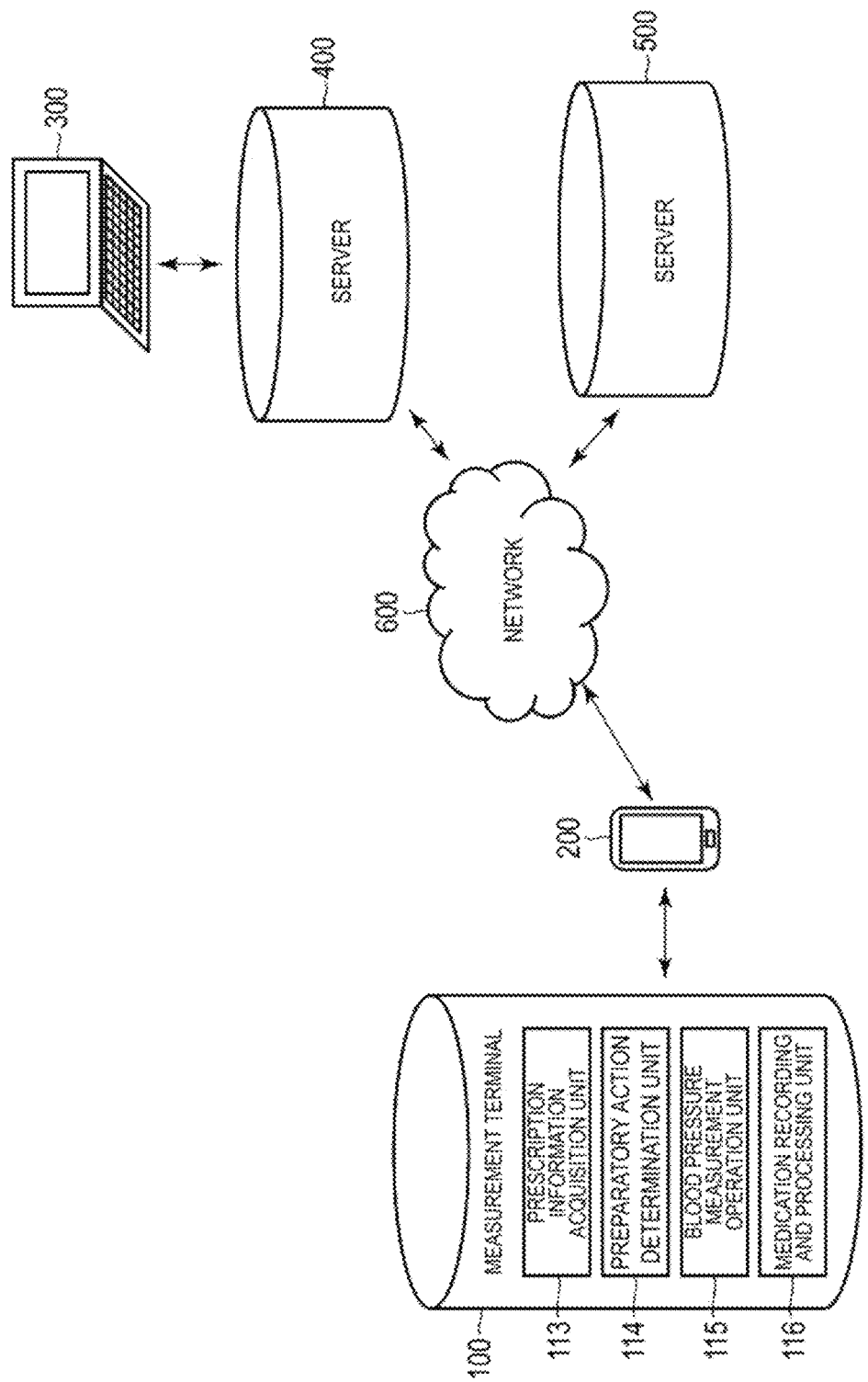
FIG. 1 is a drawing schematically illustrating an example of an application scenario of a medication management system according to an embodiment.

First, an example of a scenario to which the present invention is applied will be described using FIG. 1. FIG. 1 is a drawing schematically illustrating an example of an application scenario of a medication management system according to an embodiment.

As illustrated in FIG. 1, the medication management system includes a measurement terminal (blood pressure measurement device) 100, a user terminal 200, a medical practitioner terminal 300, and servers 400, 500.

In the medication management system illustrated in FIG. 1, the measurement terminal 100 is, for example, wirelessly connected to the user terminal 200. The user terminal 200 and the servers 400, 500 are connected to each other via a wide area network 600. Further, the server 400 is connected to the medical practitioner terminal 300 via a local network (not illustrated). Note that the configuration of the medication management system is not limited to the configuration illustrated in FIG. 1.

For example, the measurement terminal 100 may be connected to the servers 400, 500 without passing through the user terminal 200. Further, a portion of the functions (processing) achieved by the measurement terminal 100 may be implemented by the user terminal 200.

The measurement terminal 100 is, for example, an upper arm electronic blood pressure monitor. The measurement terminal 100 measures biological information such as a blood pressure value of the user. Further, the measurement terminal 100 includes an operation button (a medication confirmation button) and has functions of a medication management device.

The measurement terminal 100 includes a prescription information acquisition unit 113, a preparatory action determination unit 114, a blood pressure measurement operation unit 115, and a medication recording and processing unit 116. The prescription information acquisition unit 113 acquires prescription information on the user acquired by the user terminal 200. Note that the prescription information acquisition unit 113 may acquire the prescription information directly. The preparatory action determination unit 114 determines whether or not a preparatory action for blood pressure measurement has been performed. The blood pressure measurement operation unit 115, when the operation button is operated with the preparatory action determined to have been performed, performs a blood pressure measurement operation. The medication recording and processing unit 116, when the operation button is operated (for example, pressed once) with the preparatory action not having been performed, assesses the operation as a medication confirmation operation. Then, the medication recording and processing unit 116 generates and records medication information on the basis of the acquired prescription information.

The user terminal 200 is, for example, an information communication terminal utilized by individual users, and is constituted by, for example, a portable information communication terminal such as a smart phone, a mobile phone, a tablet personal computer (PC), or a notebook PC. The user terminal 200 transfers the biological information measured by the measurement terminal 100 to the servers 400, 500. Further, the user terminal 200 acquires the prescription information and transmits the information to the measurement terminal 100. Further, the user terminal 200 receives the medication information recorded by the measurement terminal 100 and transmits the information to the servers 400, 500. Further, the user terminal 200 may display the medication information.

The medical practitioner terminal 300 is an information communication device used by a medical practitioner (a doctor, a pharmacist, or the like), and is constituted by, for example, a desktop PC, a notebook PC, or a tablet PC. The prescription information is input into the medical practitioner terminal 300 in accordance with an operation by the medical practitioner.

The server 400 is a server used by a hospital, for example. The server 400 manages the medication information on the user transmitted from the user terminal 200. Further, the medication information may be transmitted to the medical practitioner terminal 300 and confirmed by the medical practitioner.

The server 500 is a server used by an insurance company, for example. The server 500 determines the medication information on the user transmitted from the user terminal 200, and performs discount processing of an insurance premium in accordance with a determination result, and the like.

As described above, according to the measurement terminal 100, when the operation button is operated with the preparatory action for blood pressure measurement not having been performed, the operation is assessed as the medication confirmation operation. In this case, the medication information is generated and recorded on the basis of the acquired prescription information. At this time, the operation of the operation button is performed by, for example, pressing the operation button once. That is, a complicated operation by the user is not required, and the medication information can be easily recorded.

2 Configuration Example
Hardware Configuration
Measurement Terminal 100

Figure 2:
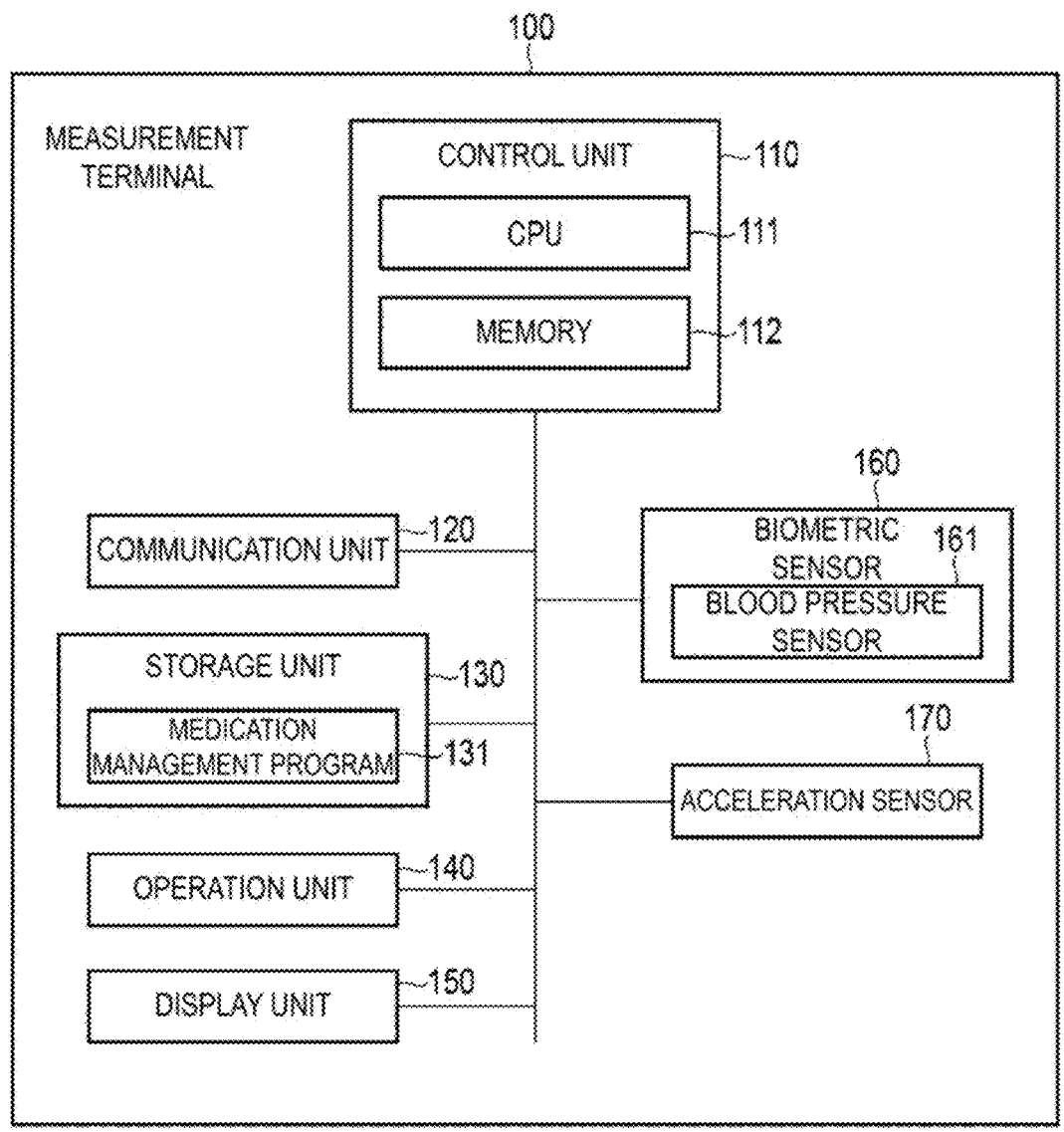
FIG. 2 is a block diagram schematically illustrating an example of a hardware configuration of a measurement terminal according to an embodiment.

Next, an example of a hardware configuration of the measurement terminal 100 according to the present embodiment will be described using FIG. 2. FIG. 2 is a block diagram schematically illustrating an example of the hardware configuration of the measurement terminal 100 according to an embodiment.

As illustrated in FIG. 2, the measurement terminal 100 according to the present embodiment includes a control unit 110, a communication unit 120, a storage unit 130, an operation unit 140, a display unit 150, a biometric sensor 160, and an acceleration sensor 170.

The control unit 110 includes a Central Processing Unit (CPU) 111 and a memory 112. The memory 112 includes a Random Access Memory (RAM) and a Read Only Memory (ROM). The memory 112 stores programs executed by the CPU 111 and functions as a working memory. The control unit 110 performs various operation controls, data processing, and the like when the CPU 111 executes a program using the memory 112.

The communication unit 120 is a communication interface for communicating with the user terminal 200. The communication unit 120 transmits data to the user terminal 200 and receives data from the user terminal 200. The communication by the communication unit 120 may be wireless communication or wired communication. In the present embodiment, the communication unit 120 is described on the basis of the assumption that the communication unit 120 communicates with the user terminal 200 by near-field wireless communication. However, the communication unit 120 is not limited thereto, and may communicate using a communication cable, or may communicate via a network such as a Local Area Network (LAN).

The storage unit 130 stores a medication management program 131 executed by the control unit 110. Further, the storage unit 130 stores the prescription information and the medication information. Further, the storage unit 130 stores a program for controlling the measurement terminal 100, configuration data for configuring various functions of the measurement terminal 100, measurement data measured by the biometric sensor 160 and the acceleration sensor 170, and the like. Further, the storage unit 130 may be used as a working memory when a program is executed.

The operation unit 140 detects an operation by the user and outputs an operation signal indicating operation content to the control unit 110. Further, the operation unit 140 includes, for example, an operation button and a power button. The operation button is a button for, by being pressed by the user with the preparatory action for blood pressure measurement not having been performed, confirming that the user has taken medicine. The operation button is preferably pressed immediately after medication, but may be pressed immediately before medication or at the time of medication. With the pressing of the operation button, medication confirmation information, including information such as a medication time period, is generated. The medication time period is calculated from a time period in which an operation button 140B is pressed, on the basis of time period information from a timepiece unit (not illustrated).

The display unit 150 includes a display screen (for example, a Liquid Crystal Display (LCD), an Electroluminescence (EL) display, or the like) and an indicator. The display unit 150 displays predetermined information in accordance with a control signal from the control unit 110. Further, the display unit 150 displays medication related information, such as medication information (medication history) and a medication message that prompts medication, for example.

The biometric sensor 160 measures the biological information on the user. For example, the biometric sensor 160 includes a blood pressure sensor 161. The blood pressure sensor 161 measures a blood pressure value as the biological information on the user. The blood pressure sensor 161 is a blood pressure sensor not capable of continuous measurement (hereinafter referred to as a non-continuous blood pressure sensor). A non-continuous blood pressure sensor measures the blood pressure of the user using a cuff as a pressure sensor (oscillometric method), for example. A non-continuous blood pressure sensor (in particular, an oscillometric method based blood pressure sensor) tends to have high measurement accuracy compared to a continuous blood pressure sensor. The following describes, by way of example, a blood pressure sensor that uses a cuff as the pressure sensor.

Note that the blood pressure sensor 161 may include a continuous blood pressure sensor. A continuous blood pressure sensor continuously measures values of blood pressure (for example, a systolic blood pressure and a diastolic blood pressure). A continuous blood pressure sensor continuously measures a blood pressure per beat, but is not limited thereto. For example, as a continuous blood pressure sensor, a blood pressure sensor based on a pulse transit time (PTT) method, a tonometry method, an optical method, an electromagnetic wave method, an ultrasonic method, or the like can be applied. The PTT method is a method of measuring pulse transit time and estimating the blood pressure value from the measured pulse transit time. The tonometry method is a method of bringing a pressure sensor into direct contact with a biological site through which an artery, such as a wrist radial artery, passes, and using information detected by the pressure sensor to measure the blood pressure value. The optical method, the electromagnetic wave method, and the ultrasonic method are methods of emitting light, an electromagnetic wave, or an ultrasonic wave to a blood vessel, and measuring the blood pressure value from a reflected wave thereof.

Further, by including a sensor other than the blood pressure sensor 161, the biometric sensor 160 can measure, as the biological information, pulse wave information, pulse information, electrocardiogram information, beat information, and body temperature information in addition to the blood pressure value.

The acceleration sensor 170 measures an acceleration experienced by the measurement terminal 100. For example, the acceleration sensor 170 measures 3-axis or 6-axis acceleration.

Figure 3:
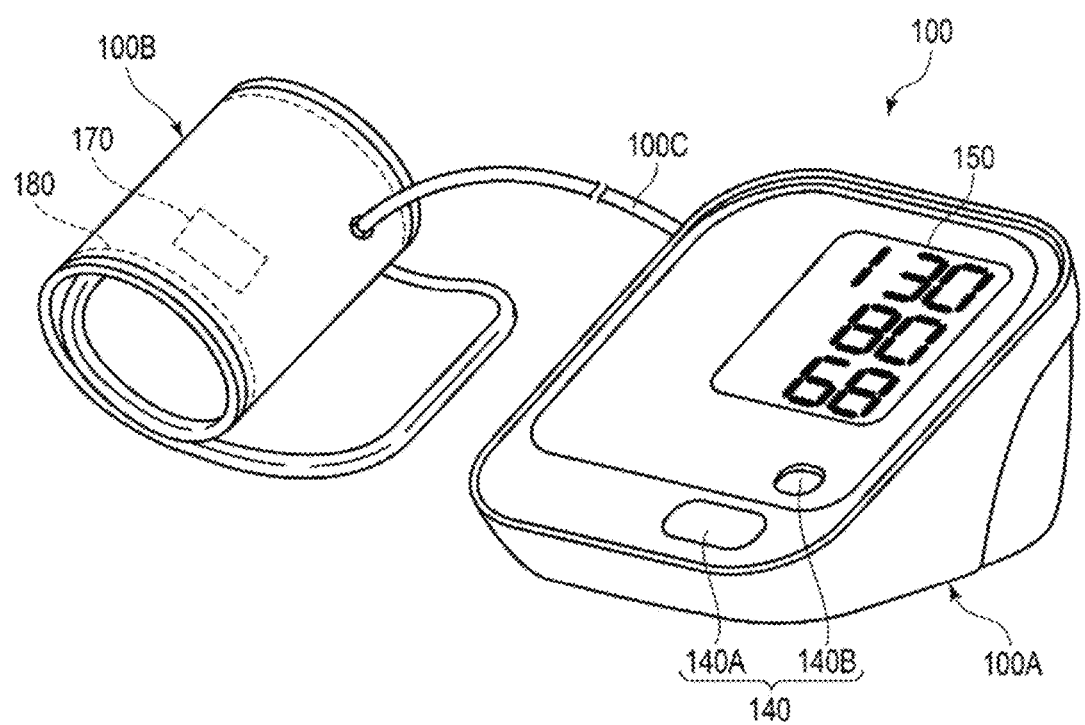
FIG. 3 is a perspective view schematically illustrating an example of an appearance of a measurement terminal according to an embodiment.

Next, an example of an appearance of the measurement terminal 100 according to the present embodiment will be described using FIG. 3. FIG. 3 is a perspective view schematically illustrating an example of the appearance of the measurement terminal 100 according to an embodiment.

As illustrated in FIG. 3, the measurement terminal 100 is, for example, an upper arm electronic blood pressure monitor. The measurement terminal 100 includes a body 100A, a cuff 100B, and a tube 100C.

The body 100A includes the display unit 150 and the operation unit 140. The display unit 150 displays the measured blood pressure value, for example. Further, the display unit 150 displays medication related information, such as medication information (medication history) and a medication message that prompts medication, for example. The operation unit 140 includes a power button 140A and the operation button 140B, for example.

The power button 140A receives an instruction to turn the power on or off. Further, the power button 140A receives an instruction to prepare for blood pressure measurement. That is, when the power button 140A is pressed, the preparatory action for blood pressure measurement is determined to have been performed.

On the other hand, when the operation button 140B is operated (pressed once) with the preparatory action for blood pressure measurement having been performed, the operation button 140B receives an instruction to start blood pressure measurement. Further, when the operation button 140B is operated (pressed once) with the preparatory action for blood pressure measurement not having been performed, the operation button 140B receives an instruction to record the medication information. That is, the operation button 140B is a button for, by being pressed by the user with the preparatory action for blood pressure measurement not having been performed, confirming that the user has taken medicine. The operation button 140B is preferably pressed immediately after medication, but may be pressed immediately before medication or at the time of medication. In a case where the operation button 140B is pressed, the medication confirmation information, including information such as the medication time period, is generated. The medication time period is calculated from a time period in which the operation button 140B is pressed, on the basis of the time period information from the timepiece unit (not illustrated).

The operation unit 140 is provided as a hardware button, that is, a button that is a physical component, rather than as a software button such as a touch panel.

The cuff 100B is provided with the acceleration sensor 170 and a fluid bag 180. The acceleration sensor 170 detects an acceleration of a target measurement site of the user. The fluid bag 180 compresses the target measurement site of the user. The cuff 100B is attached to an upper arm of the user, and thus the blood pressure value of the user is measured. Further, when the cuff 100B is attached to the upper arm of the user, the preparatory action for blood pressure measurement is determined to have been performed by detection of an acceleration by the acceleration sensor 170.

The tube 100C is flexible and connects the cuff 100B and the body 100A. Air is fed into the fluid bag 180 from a pump (not illustrated) provided in an interior of the body 100A, via this tube 100C.

In the case where blood pressure is measured in accordance with a typical oscillometric method, operations such as the following are performed. First, the cuff 100B is wrapped in advance around the target measurement site (for example, the upper arm) of the user. Once measurement is initiated, the pump and a valve (not illustrated) are controlled to increase the cuff pressure above a systolic blood pressure and subsequently gradually reduce the pressure. In this process of reducing the pressure, the cuff pressure is detected, and a fluctuation in arterial volume produced in the artery at the target measurement site is extracted as a pulse wave signal. The systolic blood pressure and the diastolic blood pressure are calculated on the basis of a change (mainly rising and falling) in amplitude of a pulse wave signal associated with the change in cuff pressure at this time.

User Terminal 200

Figure 4:
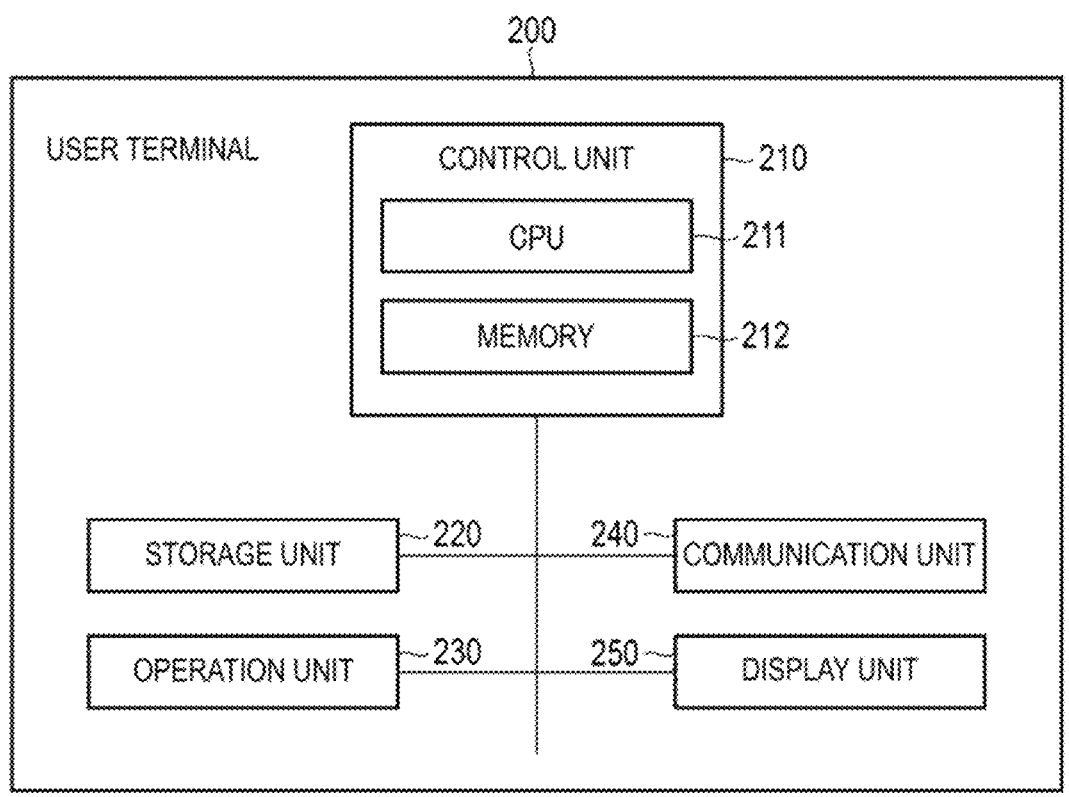
FIG. 4 is a block diagram schematically illustrating an example of a hardware configuration of a user terminal according to an embodiment.

Next, an example of a hardware configuration of the user terminal 200 according to the present embodiment will be described using FIG. 4. FIG. 4 is a block diagram schematically illustrating an example of the hardware configuration of the user terminal 200 according to an embodiment.

As illustrated in FIG. 4, the user terminal 200 according to the present embodiment includes a control unit 210, a storage unit 220, an operation unit 230, a communication unit 240, and a display unit 250.

The control unit 210 includes a CPU 211 and a memory 212. The memory 212 includes a RAM and a ROM. The memory 212 stores programs executed by the CPU 211 and functions as a working memory. The control unit 210 performs various operation controls, data processing, and the like when the CPU 211 executes a program using the memory 212. Further, the control unit 210 may capture a prescription with a camera or the like (not illustrated), and read and acquire the prescription information from the captured prescription. Further, the control unit 210 may download and acquire the prescription information on the basis of an input by the medical practitioner or the like.

The storage unit 220 is an auxiliary storage device such as, for example, a hard disk drive or a solid state drive, and stores the programs executed by the control unit 210. Further, the storage unit 220 may store data generated by the measurement terminal 100 and the like. Further, the storage unit 220 may store display data displayed on the display unit 250 and the like. Further, the storage unit 220 may store the prescription information and the medication information.

The operation unit 230 includes a touch panel provided on the display screen of the display unit 250, for example. The operation unit 230 is not limited thereto, and may include an operation button, a keyboard, and a mouse. The operation unit 230 detects an operation by the user and outputs an operation signal indicating operation content to the control unit 210.

The communication unit 240 is a communication interface for communicating with the measurement terminal 100 and the servers 400, 500. The communication unit 240 transmits data to the measurement terminal 100 and receives data from the measurement terminal 100. Further, the communication unit 240 transmits data to the servers 400, 500 and receives data from the servers 400, 500 via the network 600. The communication by the communication unit 240 may be wireless communication or wired communication. In the present embodiment, descriptions are made on the basis of the assumption that the network is, for example, the Internet or the like, but the network is not limited thereto. The network may be another type of network such as a LAN, or a one-to-one communication using a communication cable such as a universal serial bus (USB) cable or the like.

The display unit 250 includes a display screen (for example, an LCD, an EL display, or the like). The display unit 250 displays information in accordance with a control signal from the control unit 210. The display unit 250 may display medication related information, such as the medication information (medication history) and a medication message that prompts medication instead of the display unit 150 of the measurement terminal 100.

Medical Practitioner Terminal 300

Figure 5:
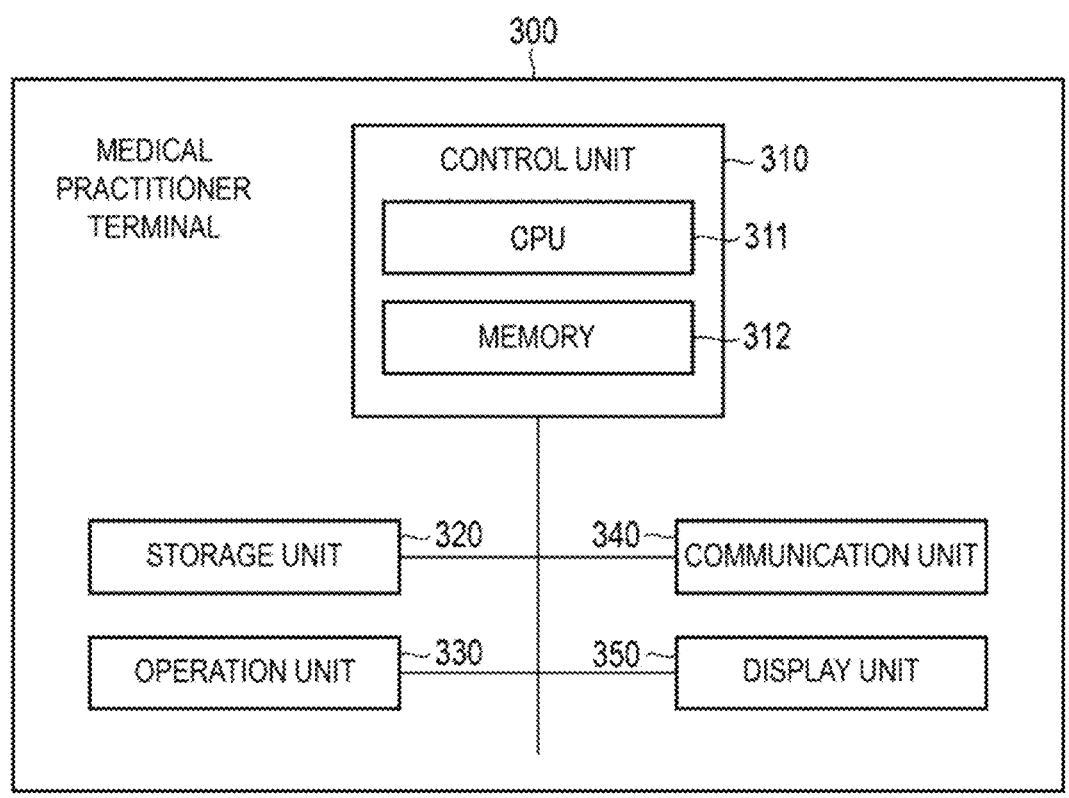
FIG. 5 is a block diagram schematically illustrating an example of a hardware configuration of a medical practitioner terminal according to an embodiment.

Next, an example of a hardware configuration of the medical practitioner terminal 300 according to the present embodiment will be described using FIG. 5. FIG. 5 is a block diagram schematically illustrating an example of the hardware configuration of the medical practitioner terminal 300 according to an embodiment.

As illustrated in FIG. 5, the medical practitioner terminal 300 according to the present embodiment includes a control unit 310, a storage unit 320, an operation unit 330, a communication unit 340, and a display unit 350.

The control unit 310 includes a CPU 311 and a memory 312. The memory 312 includes a RAM and a ROM. The memory 312 stores programs executed by the CPU 311 and functions as a working memory. The control unit 310 performs various operation controls, data processing, and the like when the CPU 311 executes a program using the memory 312.

The storage unit 320 is an auxiliary storage device such as, for example, a hard disk drive or a solid state drive, and stores the programs executed by the control unit 310. The storage unit 320 may store the prescription information and the medication information.

The operation unit 330 includes a touch panel provided on the display screen of the display unit 350, for example. The operation unit 330 is not limited thereto, and may include an operation button, a keyboard, and a mouse. The operation unit 330 detects an operation by the medical practitioner and outputs an operation signal indicating operation content to the control unit 310.

The communication unit 340 is a communication interface for communicating with the server 400. The communication unit 340 transmits data to the server 400 and receives data from the server 400. The communication by the communication unit 340 may be wireless communication or wired communication. In the present embodiment, description is made on the basis of the assumption that the communication unit 340 communicates with the server 400 via another type of network such as a LAN, but the communication unit 340 is not limited thereto, and may include a unit that performs communication serially using a communication cable.

The display unit 350 includes a display screen (for example, an LCD, an EL display, or the like). The display unit 350 displays information in accordance with a control signal from the control unit 310.

Server 400

Figure 6:
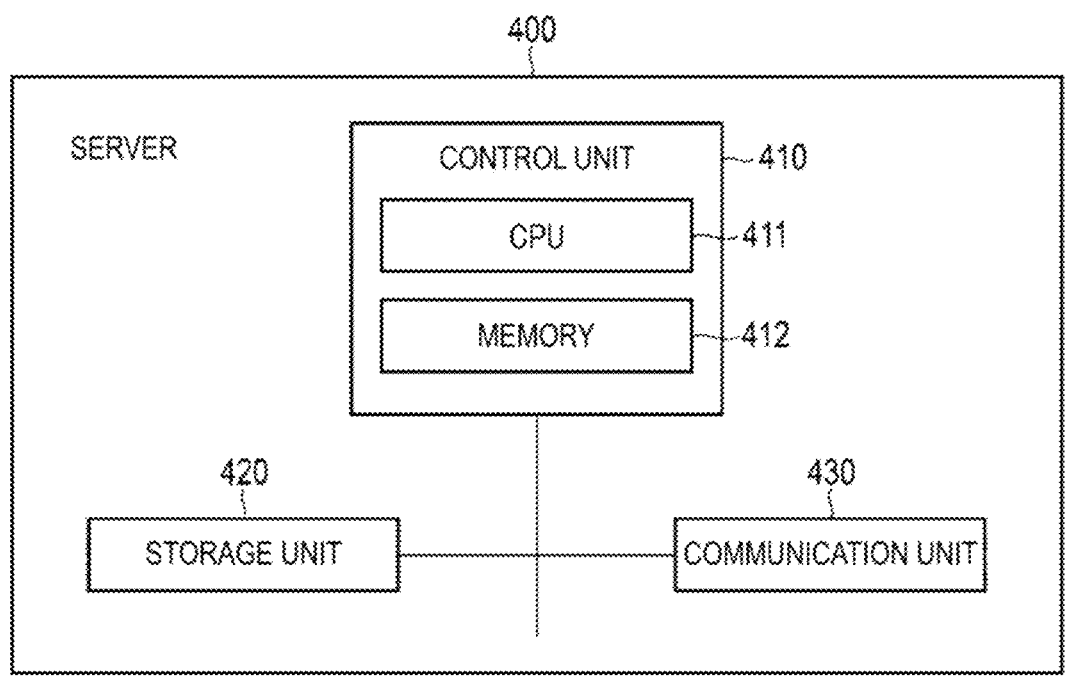
FIG. 6 is a block diagram schematically illustrating an example of a hardware configuration of a server according to an embodiment.

Next, an example of a hardware configuration of the server 400 according to the present embodiment will be described using FIG. 6. FIG. 6 is a block diagram schematically illustrating an example of the hardware configuration of the server 400 according to an embodiment.

As illustrated in FIG. 6, the server 400 according to the present embodiment includes a control unit 410, a storage unit 420, and a communication unit 430.

The control unit 410 includes a CPU 411 and a memory 412. The memory 412 includes a RAM and a ROM. The memory 412 stores programs executed by the CPU 411 and functions as a working memory. The control unit 410 performs various operation controls, data processing, and the like when the CPU 411 executes a program using the memory 412.

The storage unit 420 is an auxiliary storage device such as, for example, a hard disk drive or a solid state drive, and stores the programs executed by the control unit 410.

The communication unit 430 is a communication interface for communicating with the user terminal 200, the medical practitioner terminal 300, and the server 500. The communication unit 430 transmits data to the medical practitioner terminal 300 and receives data from the medical practitioner terminal 300 via the local network. Further, the communication unit 430 transmits data to the user terminal 200 and the server 500 and receives data from the user terminal 200 and the server 500 via the network 600. The communication by the communication unit 430 may be wireless communication or wired communication.

Server 500

Figure 7:
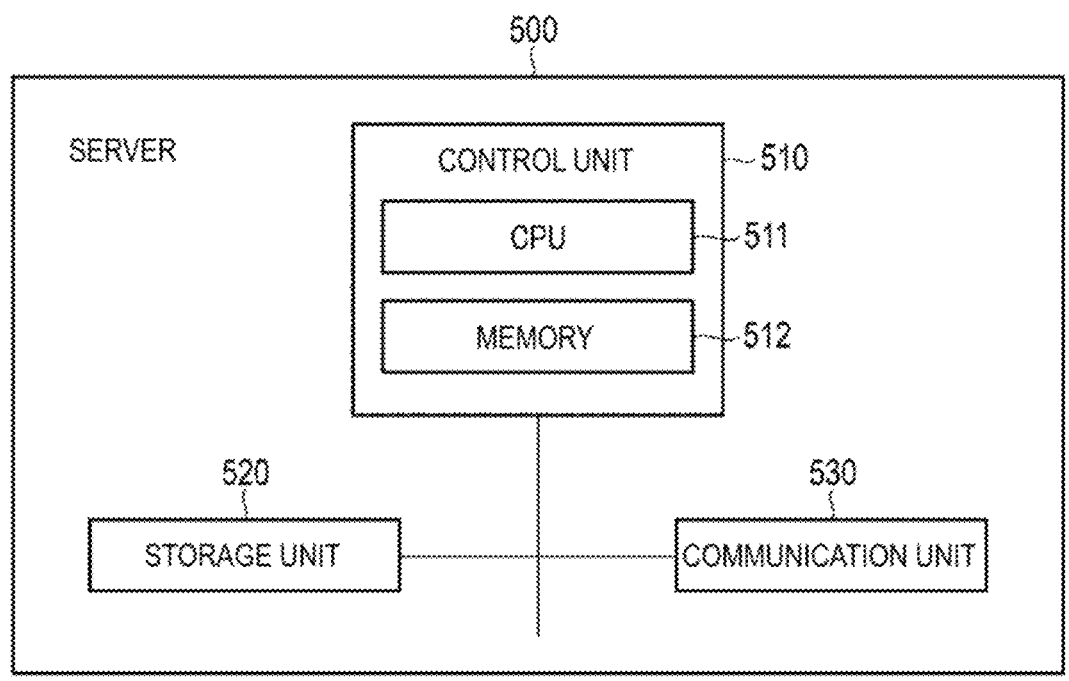
FIG. 7 is a block diagram schematically illustrating an example of a hardware configuration of a server according to an embodiment.

Next, an example of a hardware configuration of the server 500 according to the present embodiment will be described using FIG. 7. FIG. 7 is a block diagram schematically illustrating an example of the hardware configuration of the server 500 according to an embodiment.

As illustrated in FIG. 7, the server 500 according to the present embodiment includes a control unit 510, a storage unit 520, and a communication unit 530. The control unit 510 includes a CPU 511 and a memory 512.

The control unit 510, the storage unit 520, the communication unit 530, the CPU 511, and the memory 512 are the same as the control unit 410, the storage unit 420, the communication unit 430, the CPU 411, and the memory 412 of the server 400, respectively.

Functional Configuration

Measurement Terminal 100

Figure 8:
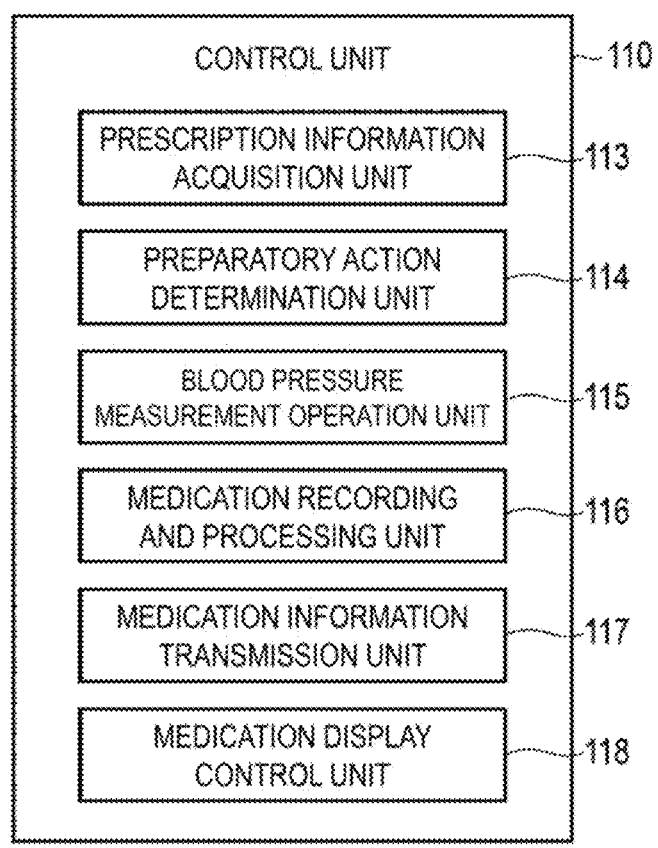
FIG. 8 is a block diagram schematically illustrating an example of a functional configuration of a control unit of a measurement terminal according to an embodiment.

Next, an example of a functional configuration of the control unit 110 of the measurement terminal 100 according to the present embodiment will be described using FIG. 8. FIG. 8 is a block diagram schematically illustrating an example of the functional configuration of the control unit 110 of the measurement terminal 100 according to an embodiment.

The control unit 110 of the measurement terminal 100 copies the medication management program 131 stored in the storage unit 130 in the memory 112. Then, the control unit 110 causes the CPU 111 to interpret and execute the medication management program 131 copied in the memory 112 to control each component. Accordingly, as illustrated in FIG. 8, the control unit 110 of the measurement terminal 100 according to the present embodiment functions as the prescription information acquisition unit 113, the preparatory action determination unit 114, the blood pressure measurement operation unit 115, the medication recording and processing unit 116, the medication information transmission unit 117, and the medication display control unit 118.

The prescription information acquisition unit 113 acquires the prescription information on the user from the user terminal 200. The prescription information corresponds to a medication instruction from the medical practitioner and is acquired by the user terminal 200. The user terminal 200 may, for example, capture a prescription with a camera or the like (not illustrated), and read and acquire the prescription information from the captured prescription. Further, the user terminal 200 may, for example, read and acquire the prescription information from a barcode or Quick Response (QR) code (trademark) using a camera (not illustrated) or the like. Further, the user terminal 200 may download and acquire the prescription information on the basis of an input by the medical practitioner or the like. Note that the prescription information acquisition unit 113 may acquire the prescription information directly by the same method as that of the user terminal 200.

FIG. 9 is a drawing illustrating an example of prescription information according to an embodiment.

As illustrated in FIG. 9, the prescription information includes, for example, information such as a type, a time period, and a dose. The type indicates a type of prescribed medicine. The time period indicates a time period in which the prescribed medicine should be taken. The dose indicates a dose that should be taken at one time for the prescribed medicine.

In FIG. 9, for example, medicines A, B, C are prescribed. The medicine A is a medicine to be taken in an amount of one tablet in the morning. The medicine B is a medicine to be taken in amount of two tablets in each of the morning and the evening. The medicine C is a medicine to be taken in an amount of two tablets before bed.

Again, as illustrated in FIG. 8, the preparatory action determination unit 114 determines whether or not the preparatory action for blood pressure measurement has been performed. The preparatory action determination unit 114 determines whether or not the preparatory action of blood pressure measurement has been performed in accordance with, for example, operation (pressing) or non-operation (non-pressing) of the power button 140A. Further, the preparatory action determination unit 114 determines whether or not the preparatory action of blood pressure measurement has been performed in accordance with, for example, use or non-use of the cuff 100B.

The blood pressure measurement operation unit 115 performs the blood pressure measurement operation when the operation button 140B is operated (pressed) with the preparatory action of blood pressure measurement determined to have been performed by the preparatory action determination unit 114. That is, the blood pressure measurement operation unit 115 performs the blood pressure measurement operation when the operation button 140B is operated (pressed) with the power button 140A having been operated. Alternatively, the blood pressure measurement operation unit 115 performs the blood pressure measurement operation when the operation button 140B is operated (pressed) with the cuff 100B having been used.

When the operation button is operated (for example, pressed once) with the preparatory action for blood pressure measurement not having been performed, the medication recording and processing unit 116 assesses that the operation is the medication confirmation operation. Then, the medication recording and processing unit 116 determines the medication confirmation information input by the operation of the operation unit 140. The medication confirmation information is information input by the operation button 140B being pressed once by the user with the preparatory action for blood pressure measurement not having been performed, and includes, for example, information on the medication time period. The medication time period is calculated from a time period in which the operation button 140B is pressed, on the basis of the time period information from the timepiece unit (not illustrated). Then, the medication recording and processing unit 116 reads the corresponding prescription drug information from the acquired prescription information on the basis of the determination result of the medication confirmation information (medication time period). The prescription drug information includes information on the type and the dose of the prescribed medicine.

More specifically, in a case where the time period in which the operation button 140B is pressed is morning, the medication recording and processing unit 116 reads the prescription drug information corresponding to morning (information on the type and the dose of medicine to be taken in the morning). For example, according to the prescription information illustrated in FIG. 9, the medication recording and processing unit 116 reads one tablet of the medicine A and two tablets of the medicine B as the prescription drug information corresponding to morning. Further, in a case where the time period in which the operation button 140B is pressed is evening, the medication recording and processing unit 116 reads the prescription drug information corresponding to evening (information on the type and the dose of medicine to be taken in the evening). For example, according to the prescription information illustrated in FIG. 9, the medication recording and processing unit 116 reads two tablets of the medicine B as the prescription drug information corresponding to evening. Further, in a case where the time period in which the operation button 140B is pressed is other than morning and evening, the medication recording and processing unit 116 reads the prescription drug information corresponding to other than morning and evening (for example, before bed; information on the type and the dose of medicine to be taken before bed). For example, according to the prescription information illustrated in FIG. 9, the medication recording and processing unit 116 reads two tables of the medicine C as the prescription drug information corresponding to before bed.

Note that, while, for example, morning is configured as 5:00 to 9:00 and evening is configured as 17:00 to 21:00, these can be configured as desired.

Furthermore, the medication recording and processing unit 116 generates and records the medication information on the basis of the input medication confirmation information and the read prescription drug information. That is, the medication recording and processing unit 116 records information on the type and the dose of the medicine of the prescription drug information in association with the medication time period (the medication date and time) of the medication confirmation information.

FIG. 10 is a drawing illustrating an example of the medication information according to an embodiment.

As illustrated in FIG. 10, the medication information includes, for example, a type of medicine taken, a date and a time taken, and a dose of the medicine taken.

In FIG. 10, one tablet of the medicine A and two tablets of the medicine B were taken at 7:20 on 2017/10/5, two tablets of the medicine B were taken at 19:15 on 2017/10/5, and two tablets of the medicine C were taken at 22:10 on 2017/10/5.

Note that the medication information is not limited thereto. For example, a remaining amount of a prescription drug may be calculated on the basis of this medication history. Further, medicine for lowering blood pressure need not be taken when, for example, the blood pressure is sufficiently low. In such a case, the fact that the medication was intentionally not taken may be recorded as the medication information.

The medication information transmission unit 117 transmits the medication information to the user terminal 200. The medication information may be displayed on the display unit 250 of the user terminal 200. The user terminal 200 transmits the medication information from the measurement terminal 100 (medication information transmission unit 117) to the servers 400, 500. The server 400 used by the hospital manages the medication information on the user transmitted from the user terminal 200. Further, the medication information may be transmitted to the medical practitioner terminal 300 and confirmed by the medical practitioner. The server 500 used by the insurance company determines the medication information on the user transmitted from the user terminal 200, and performs discount processing of an insurance premium in accordance with the determination result, and the like.

Note that the medication information transmission unit 117 may transmit the medication information directly to the servers 400, 500. That is, the medication information transmission unit 117 transmits the medication information to external devices including the user terminal 200 and the servers 400, 500.

The medication display control unit 118 performs control such that the display unit 150 displays the information related to medication. The information related to medication includes, for example, the medication information (medication history) and a medication message that prompts medication. More specifically, the medication display control unit 118 causes the display unit 150 to display the medication information in accordance with an input to the operation unit 140 by the user, for example. Further, the medication display control unit 118 causes the display unit 150 to display a medication message that prompts medication when the medication time is reached, for example.

3 Operation Example

Measurement Terminal 100

Figure 11:
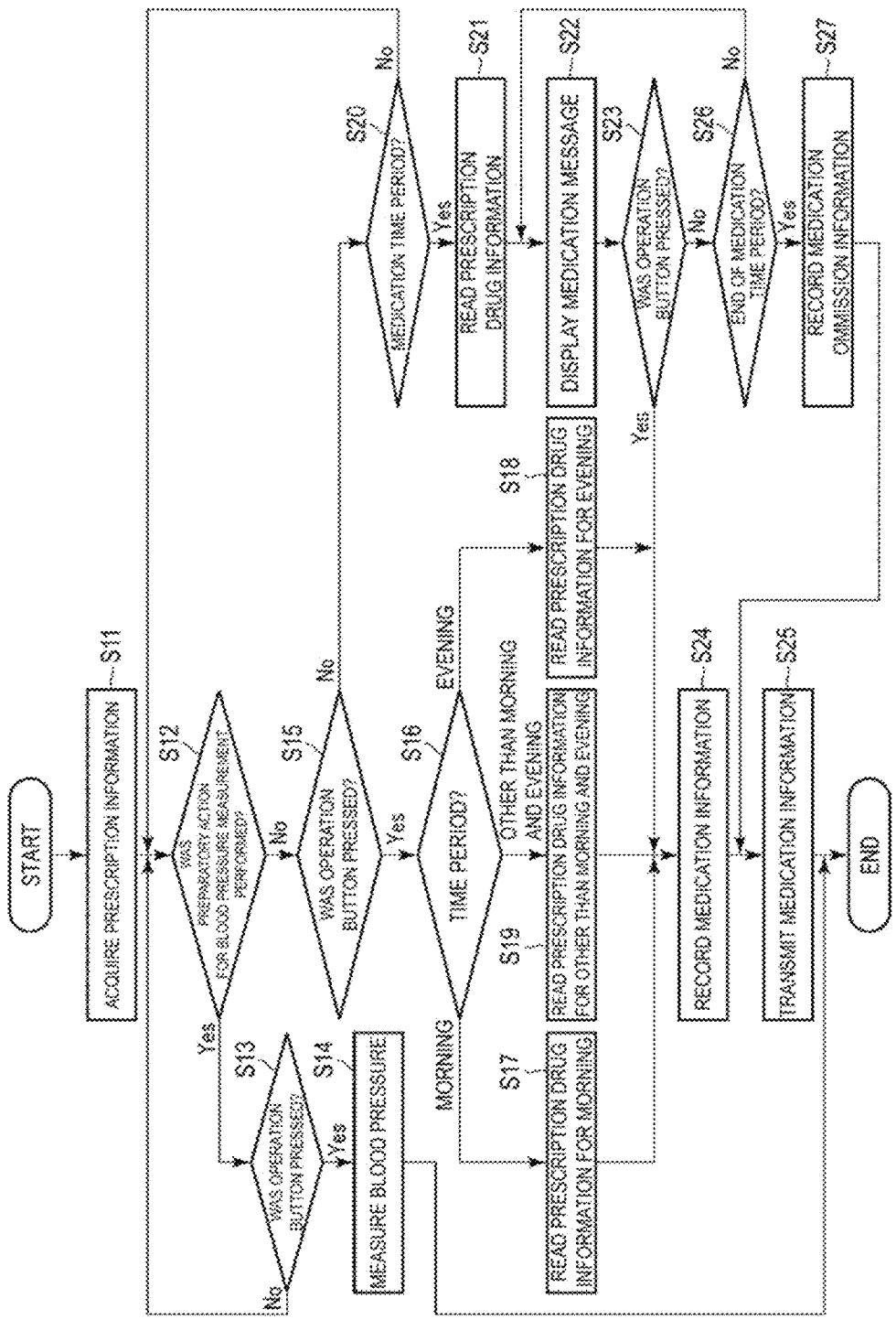
FIG. 11 is a flowchart illustrating an example of a processing procedure of a blood pressure measurement device according to an embodiment.

Next, an operation example of the measurement terminal 100 will be described using FIG. 11. FIG. 11 is a flowchart illustrating an example of a processing procedure of the measurement terminal 100. Note that the processing procedure described below is merely an example, and each of the processes may be changed to the extent possible. Further, in the processing procedure described below, steps can be omitted, substituted, and added as appropriate in accordance with the embodiment.

Step S11

In step S11, the control unit 110 functions as the prescription information acquisition unit 113, and acquires the prescription information on the user from the user terminal 200.

Step S12

In step S12, the control unit 110 functions as the preparatory action determination unit 114, and determines whether or not the preparatory action for blood pressure measurement has been performed. Then, in a case where the preparatory action has been performed in step S12, the processing proceeds to step S13. On the other hand, in a case where the preparatory action has not been performed in step S12, the processing proceeds to step S15.

Step S13

In step S13 following step S12, the control unit 110 functions as the blood pressure measurement operation unit 115, and determines whether or not the operation button 140B was pressed. Then, in a case where the operation button 140B was pressed in step S13, the processing proceeds to step S14. On the other hand, in a case where the operation button 140B has not been pressed in step S13, the processing proceeds to step S12 after a predetermined amount of time has elapsed.

Step S14

In step S14 following step S13, the control unit 110 functions as the blood pressure measurement operation unit 115, and performs the blood pressure measurement operation.

Step S15

In step S15 following step S12, the control unit 110 functions as the medication recording and processing unit 116. In step S15, the control unit 110 determines whether or not the operation button 140B was pressed by the user. That is, the control unit 110 determines whether or not the medication confirmation information was input by the user. Then, in a case where the operation button 140B was pressed in step S15, the control unit 110 assesses that the operation is the medication confirmation operation, and the processing proceeds to step S16. On the other hand, in a case where the operation button 140B was not pressed in step S15, the processing proceeds to step S20.

Step S16

In step S16 following step S15, the control unit 110 functions as the medication recording and processing unit 116. In step S16, the control unit 110 determines the medication time period of the medication confirmation information input by the operation of the operation button 140B. That is, the time period in which the operation button 140B was pressed is determined. Then, in a case where the medication time period is morning in step S16, the processing proceeds to step S17. Further, in a case where the medication time period is evening in step S16, the processing proceeds to step S18. Further, in a case where the medication time period is other than morning and evening in step S16, the processing proceeds to step S19.

Steps S17, S18, and S19

In steps S17, S18, and S19 following step S16, the control unit 110 functions as the medication recording and processing unit 116. In step S17, the control unit 110 reads the prescription drug information corresponding to morning. In step S18, the control unit 110 reads the prescription drug information corresponding to evening. In step S19, the control unit 110 reads the prescription drug information corresponding to other than morning and evening.

Note that in cases where there is no corresponding prescription drug information in steps S17, S18, and S19, the medication by the user is assessed as an error. In this case, the control unit 110 may cause the display unit 150 to display a medication error message.

Step S20

In step S20 following step S15, the control unit 110 functions as the medication recording and processing unit 116. In step S20, the control unit 110 determines whether or not the current time is a medication time period. In a case where the current time is a medication time period in step S20, the processing proceeds to step S21. On the other hand, in a case where the current time is not a medication time period in step S20, the processing proceeds to step S12.

Step S21

In step S21 following step S20, the control unit 110 functions as the medication recording and processing unit 116. In step S21, the control unit 110 reads the prescription drug information corresponding to the medication time period including the current time. More specifically, the control unit 110 reads the prescription drug information corresponding to morning when the current time is morning, reads the prescription drug information corresponding to evening when the current time is evening, and reads the prescription drug information corresponding to other than morning and evening when the current time is other than morning and evening.

Step S22

In step S22 following step S21, the control unit 110 functions as the medication display control unit 118. In step S22, the control unit 110 causes the display unit 150 to display a message that prompts medication on the basis of the read prescription drug information. The display unit 150 displays, for example, a message such as, "Take one tablet of medicine A and two tablets of medicine B" when the current time is morning.

Step S23

In step S23 following step S22, the control unit 110 functions as the medication recording and processing unit 116. In step S23, the control unit 110 determines whether or not the operation button 140B was pressed by the user. That is, the control unit 110 determines whether or not the medication confirmation information was input by the user. Then, in a case where the operation button 140B was pressed in step S23, the control unit 110 assesses that the operation is the medication confirmation operation, and the processing proceeds to step S24. On the other hand, in a case where the operation button 140B was not pressed in step S23, the processing proceeds to step S26.

Step S24

In step S24 following steps S17, S18, S19, and S23, the control unit 110 functions as the medication recording and processing unit 116. In step S24 after steps S17, S18, and S19, the control unit 110 generates and records the medication information on the basis of the medication confirmation information input in step S15 and the prescription drug information read in steps S17, S18, and S19. On the other hand, in step S24 after step S23, the control unit 110 generates and records the medication information on the basis of the prescription drug information read in step S21 and the medication confirmation information input in step S23.

Step S26

In step S26 following step S25, the control unit 110 functions as the medication recording and processing unit 116 and determines whether or not the medication time period has ended. Then, in a case where the medication time period has ended in step S26, the processing proceeds to step S27. On the other hand, in a case where the medication time period has not ended in step S26, the processing proceeds to step S22.

Step S27

In step S27 following step S26, the control unit 110 functions as the medication recording and processing unit 116, and generates and records medication omission information. The medication omission information is information indicating that the user has not taken medicine, and includes, for example, a date and a time at which the medicine was not taken.

Step S25

In step S25 following steps S24 and S27, the control unit 110 functions as the medication information transmission unit 117. In step S25, the control unit 110 transmits the medication information recorded in step S24 and the medication omission information recorded in step S27 to the user terminal 200.

4 Action and Effect

As described above, in the present embodiment, when the operation button 140B is operated with the preparatory action for blood pressure measurement not having been performed, the measurement terminal 100 assesses the operation as the medication confirmation operation. Then, the measurement terminal 100 generates and records the medication information on the basis of the acquired prescription information. At this time, the operation of the operation button 140B is performed by, for example, pressing the operation button 140B once. That is, when the medication information is recorded, a complicated operation by the user is not required. As a result, the burden on the user can be reduced and the medication information can be easily recorded.

Further, in the present embodiment, when a medication time period is reached, the measurement terminal 100 reads the corresponding prescription drug information from the prescription information on the basis of the medication time period, and a medication message that prompts medication is displayed. This makes it possible to also prevent the user from forgetting medication itself.

The present invention is not limited to the embodiments described above and can be embodied by modifying the components in an implementation stage in a range without departing from the gist thereof. Further, various inventions can be formed by appropriate combinations of the plurality of components disclosed in the embodiments described above. For example, from among all components illustrated in the embodiments, several components may be deleted. Furthermore, components of different embodiments may be combined as appropriate.

REFERENCE SIGNS LIST

100 Measurement terminal
110 Control unit
120 Communication unit
130 Storage unit
140 Operation unit
150 Display unit
160 Biometric sensor
170 Acceleration sensor
111 CPU
112 Memory
113 Prescription information acquisition unit
114 Preparatory action determination unit
115 Blood pressure measurement operation unit
116 Medication recording and processing unit
117 Medication information transmission unit
118 Medication display control unit
131 Medication management program
161 Blood pressure sensor
100A Body
100B Cuff
100C Tube
140A Power button
140B Operation button
180 Fluid bag
200 User terminal
210 Control unit
220 Storage unit
230 Operation unit 240 Communication unit
250 Display unit
211 CPU
212 Memory
300 Medical practitioner terminal
310 Control unit
320 Storage unit
330 Operation unit
340 Communication unit
350 Display unit
311 CPU
312 Memory
400 Server
410 Control unit
420 Storage unit
430 Communication unit
411 CPU
412 Memory
500 Server
510 Control unit
520 Storage unit
530 Communication unit
511 CPU
512 Memory
600 Network

The invention claimed is:

1. A blood pressure measurement device including an operation button, the blood pressure measurement device comprising:
   a processor; and
   a memory, wherein
   the processor is configured to acquire prescription information,
   the processor is configured to determine whether a preparatory action for blood pressure measurement is performed,
   the processor is configured to perform a blood pressure measurement operation in a case where the operation button is operated with the preparatory action determined to be performed, and
   the processor is configured to, in a case where the operation button is operated with the preparatory action determined not to be performed, assess that the operation is a medication confirmation operation, and generate and record medication information on the basis of the prescription information thus acquired.

2. The blood pressure measurement device according to claim 1, wherein
   in a case where the blood pressure measurement device includes a cuff, the processor is configured to determine whether the preparatory action for blood pressure measurement is performed by use or non-use of the cuff.

3. The blood pressure measurement device according to claim 1, wherein
   in a case where the blood pressure measurement device includes a power button, the processor is configured to determine whether the preparatory action for blood pressure measurement is performed by operation or non-operation of the power button.

4. The blood pressure measurement device according to claim 1, wherein
   the processor is configured to determine a time period of medication confirmation information input by operation of the operation button and read prescription drug information corresponding to the time period from the prescription information, and
   the processor is configured to record the medication information on the basis of the medication confirmation information and the prescription drug information.

5. The blood pressure measurement device according to claim 1, wherein
   the processor is configured to, in a case where a medication time period is reached with the medication confirmation operation determined not to be performed, control display of a medication message that prompts medication.

6. The blood pressure measurement device according to claim 5, wherein
   the processor is configured to record medication omission information in a case where the medication confirmation operation is not performed by an end of the medication time period.

7. The blood pressure measurement device according to claim 1, wherein
   the processor is configured to calculate a remaining amount of a prescription drug on the basis of the medication information.

8. The blood pressure measurement device according to claim 1, wherein
   the processor is configured to transmit the medication information to an external device.

9. A medication management method executed by a blood pressure measurement device including an operation button, the medication management method comprising the steps of:
   acquiring prescription information;
   determining whether a preparatory action for blood pressure measurement is performed; and
   in a case where the operation button is operated with the preparatory action determined not to be performed, assessing that the operation is a medication confirmation operation, and generating and recording medication information on the basis of the prescription information thus acquired.

10. A non-transitory storage medium storing a medication management program for causing a processor included in the blood pressure measurement device to execute each step included in the medication management method described in claim 9.

11. The blood pressure measurement device according to claim 2, wherein
   the processor is configured to calculate a remaining amount of a prescription drug on the basis of the medication information.

12. The blood pressure measurement device according to claim 3, wherein
   the processor is configured to calculate a remaining amount of a prescription drug on the basis of the medication information.

13. The blood pressure measurement device according to claim 4, wherein
   the processor is configured to calculate a remaining amount of a prescription drug on the basis of the medication information.

14. The blood pressure measurement device according to claim 5, wherein
   the processor is configured to calculate a remaining amount of a prescription drug on the basis of the medication information.

15. The blood pressure measurement device according to claim 6, wherein
   the processor is configured to calculate a remaining amount of a prescription drug on the basis of the medication information.

16. The blood pressure measurement device according to claim 2, wherein
the processor is configured to transmit the medication information to an external device.

17. The blood pressure measurement device according to claim 3, wherein
the processor is configured to transmit the medication information to an external device.

18. The blood pressure measurement device according to claim 4, wherein
the processor is configured to transmit the medication information to an external device.

19. The blood pressure measurement device according to claim 5, wherein
the processor is configured to transmit the medication information to an external device.

20. The blood pressure measurement device according to claim 6, wherein
the processor is configured to transmit the medication information to an external device.

* * * * *